United States Patent
Gu et al.

(10) Patent No.: US 9,941,894 B1
(45) Date of Patent: Apr. 10, 2018

(54) MULTIPLE STRING, MULTIPLE OUTPUT DIGITAL TO ANALOG CONVERTER

(71) Applicant: Analog Devices Global, Hamilton (BM)

(72) Inventors: Shurong Gu, Beijing (CN); Dennis A. Dempsey, Newport (IE); GuangYang Qu, Beijing (CN); Hanqing Wang, Beijing (CN); Tony Yincai Liu, Beijing (CN)

(73) Assignee: Analog Devices Global, Hamilton (BM)

( * ) Notice: Subject to any disclaimer, the term of this patent is extended or adjusted under 35 U.S.C. 154(b) by 0 days.

(21) Appl. No.: 15/586,848

(22) Filed: May 4, 2017

(51) Int. Cl.
| | |
|---|---|
| *H03M 1/66* | (2006.01) |
| *H03M 1/08* | (2006.01) |
| *H03M 1/00* | (2006.01) |
| *G01N 27/416* | (2006.01) |
| *G01N 33/00* | (2006.01) |

(52) U.S. Cl.
CPC ...... *H03M 1/0827* (2013.01); *G01N 27/4162* (2013.01); *G01N 33/004* (2013.01); *H03M 1/002* (2013.01)

(58) Field of Classification Search
CPC .. H03M 1/0827; H03M 1/002; G01N 33/004; G01N 27/4162
USPC ................................................. 341/118, 143
See application file for complete search history.

(56) References Cited

U.S. PATENT DOCUMENTS

| | | | |
|---|---|---|---|
| 4,968,946 A | 11/1990 | Maier | |
| 5,262,779 A | 11/1993 | Sauer | |
| 5,495,245 A | 2/1996 | Ashe | |
| 5,585,796 A | 12/1996 | Svensson | |
| 5,969,657 A | 10/1999 | Dempsey et al. | |
| 6,163,289 A | 12/2000 | Ginetti | |
| 6,414,616 B1 | 7/2002 | Dempsey | |
| 6,448,916 B1* | 9/2002 | Leung ................. | H03M 1/0663 341/144 |
| 6,452,405 B1 | 9/2002 | Collier-Hallman | |
| 6,778,122 B2 | 8/2004 | Lien | |
| 7,109,904 B2 | 9/2006 | Fotouhi | |
| 7,136,002 B2 | 11/2006 | Dempsey et al. | |
| 7,259,706 B2* | 8/2007 | Haurie ................. | H03M 1/682 341/144 |

(Continued)

FOREIGN PATENT DOCUMENTS

EP          1262755 A1      12/2002

OTHER PUBLICATIONS

"Analog Devices ADuDM350 Hardware Reference Manual UG-587", Rev. C, © 2014-2016, (2014-2016), 459 pgs.

(Continued)

*Primary Examiner* — Brian Young
(74) *Attorney, Agent, or Firm* — Schwegman Lundberg & Woessner, P.A.

(57) ABSTRACT

A multiple output, multiple impedance string digital-to-analog converter (DAC) circuit can provide a first output having a first resolution in response to a first digital input signal and a second output having a second resolution in response to a second digital input signal. A main impedance string and a secondary impedance string can be coupled using switching networks to provide a first DAC output. By coupling additional switches to the main impedance string and by sharing the main impedance string, a second DAC output can be realized.

20 Claims, 7 Drawing Sheets

(56) References Cited

U.S. PATENT DOCUMENTS

| | | | |
|---|---|---|---|
| 7,339,508 B2 | 3/2008 | Cosgrave et al. | |
| 7,501,970 B2 * | 3/2009 | Trifonov | H03M 1/682 |
| | | | 341/144 |
| 8,456,347 B2 | 6/2013 | Wikner | |
| 9,065,479 B2 | 6/2015 | Dempsey | |
| 9,083,380 B2 * | 7/2015 | Price | H03M 1/808 |
| 9,100,045 B2 | 8/2015 | Dempsey | |
| 9,124,296 B2 | 9/2015 | Dempsey | |
| 9,407,278 B1 | 8/2016 | Dempsey | |
| 9,444,487 B1 | 9/2016 | Dempsey | |
| 2006/0263254 A1 | 11/2006 | Lee | |
| 2012/0065540 A1 | 3/2012 | Yarden et al. | |
| 2013/0102061 A1 | 4/2013 | Coursey et al. | |

OTHER PUBLICATIONS

"Analog Devices 16-Bit Precision, Low Power Metter on a Chip with Cortex-M3 and Connectivity", © 2014 Analogy Devices, Inc., Data Sheet ADuCM350 Rev. A, (2014), 41 pgs.

"Designing a PotentioStatic Cicuit", Alphasense Application Note—AAN 105-03, (Mar. 2009), 5 pgs.

Bryant, James, et al., "Chapter 3 Data Converter Architectures", *The Data Conversion Handbook*, (2005), pp. 3.1-3.9.

\* cited by examiner

MULTIPLE STRING, MULTIPLE OUTPUT DIGITAL TO ANALOG CONVERTER

CROSS-REFERENCE TO RELATED PATENT DOCUMENTS

This patent application is related to the following applications, filed on even date herewith: U.S. patent application Ser. No. 15/586,922, entitled "SENSOR BIAS CIRCUIT FOR IMPROVED NOISE PERFORMANCE," filed on May 4, 2017, U.S. patent application Ser. No. 15/586,942, entitled "DIAGNOSTIC WAVEFORM GENERATOR FOR A SENSOR," filed on May 4, 2017, U.S. Provisional Patent Application Ser. No. 62/501,416, entitled "DIGITAL-TO-ANALOG CONVERTER (DAC) TERMINATION," filed on May 4, 2017, U.S. patent application Ser. No. 15/586,849, entitled "SYSTEMS AND METHODS FOR DETERMINING THE CONDITION OF A GAS SENSOR," filed on May 4, 2017, U.S. patent application Ser. No. 15/586,869, entitled "IMPEDANCE CHARACTERISTIC CIRCUIT FOR ELECTROCHEMICAL SENSOR," filed on May 4, 2017, U.S. patent application Ser. No. 15/586,877, entitled "INTERNAL INTEGRATED CIRCUIT RESISTANCE CALIBRATION," filed on May 4, 2017.

FIELD OF THE DISCLOSURE

This disclosure relates generally to digital to analog converters (DACs), and more particularly but not by way of limitation, to impedance string type DACs.

BACKGROUND

Real-world analog signals such as temperature, pressure, sound, or images are routinely converted to a digital representation that can be easily processed in modern digital systems. In many systems, this digital information is converted back to an analog form to perform some real-world function. The circuits that perform this step are digital-to-analog converters (DACs), and their outputs are used to drive a variety of devices. Loudspeakers, video displays, motors, mechanical servos, radio frequency (RF) transmitters, and temperature controls are just a few diverse examples. DACs are often incorporated into digital systems in which real-world signals are digitized by analog-to-digital converters (ADCs), processed, and then converted back to analog form by DACs.

A DAC produces a quantized or discrete step analog output in response to a binary digital input code and the analog output is commonly a voltage or a current. To generate the output, a reference quantity, or level, (usually the aforementioned voltage or current) is commonly divided into binary and/or linear fractions. Then the digital input drives switches that combine an appropriate number of these fractions to produce the output. The number and size of the fractions reflect the number of possible digital input codes, which is a function of converter resolution or the number of bits (n) in the input code.

SUMMARY OF THE DISCLOSURE

An electrochemical sensor can be used for various applications, such as for sensing the presence of one or more constituent gases, such as oxygen, carbon monoxide, etc., in an environment around the electrochemical sensor. The present inventors have recognized that one problem to be solved is providing a sensor, for example, with a digital-to-analog converter (DAC) circuit that is both medium-high resolution and low-power. For example, it can be desirable to increase the resolution of a DAC of a sensor to reduce quantization noise and improve accuracy. Increased DAC resolution, however, can result in the use of more switches, and thus more power consumption, particularly at higher temperatures due to leakage currents, for example. If a sensor is battery-powered, it can be desirable to lower power consumption. The present inventors have solved this problem by providing a multiple output DAC circuit that uses a shared impedance string, such as a resistor string, to generate multiple outputs having different resolutions, e.g., a first output at 12-bit resolution and a second output at a 6-bit resolution, from two digital input signals. The shared impedance string can reduce circuit complexity, thereby reducing the cost and the size of the DAC circuit, as well as reducing the leakage current, which can then be used to further reduce power consumption.

In some aspects, this disclosure is directed to a multiple output digital-to-analog converter (DAC) circuit providing at least two analog output signals of different resolution. The DAC circuit comprises a first string of first impedance elements; a second string of second impedance elements; in response to a first digital input signal, a first switching network to couple a voltage produced across at least one of the first impedance elements across the second string to a first output node, the first digital input signal comprising a first digital bit stream having most significant bits (MSBs) and least significant bits (LSBs), the second impedance elements configured to produce a first analog signal corresponding to the first digital input signal; and in response a second digital input signal, a second switching network to couple a voltage produced across at least one of the first impedance elements to a second output node, the first impedance elements configured to produce a second analog signal corresponding to the second digital input signal, wherein the first output node and the second output node form multiple outputs.

In some aspects, this disclosure is directed to a method of converting a first digital input string to a corresponding first analog signal having a first resolution and converting a second digital input string to a corresponding second analog signal having a second resolution. The method comprises providing a multiple output digital-to-analog converter (DAC) circuit, the DAC circuit comprising a first string of first impedance elements and a second string of second impedance elements; controlling, in response to a first digital input signal, a first switching network to couple a voltage produced across at least one of the first impedance elements across the second string to a first output node, the first digital input signal comprising a first digital bit stream having most significant bits (MSBs) and least significant bits (LSBs), the second impedance elements configured to produce a first analog signal corresponding to the first digital input signal; and controlling, in response to a second digital input signal, a second switching network to couple a voltage produced across at least one of the first impedance elements to a second output node, the first impedance elements configured to produce a second analog signal corresponding to the second digital input signal, wherein the first output node and the second output node form multiple outputs.

In some aspects, this disclosure is directed to an electrochemical sensing circuit comprising a multiple output digital-to-analog converter (DAC) circuit providing at least two analog output signals of different resolution. The DAC circuit comprises a first string of first impedance elements; a second string of second impedance elements; in response to a first digital input signal, a first switching network to couple a voltage produced across at least one of the first impedance elements across the second string to a first output node, the first digital input signal comprising a first digital bit stream having most significant bits (MSBs) and least significant bits (LSBs), the second impedance elements configured to produce a first analog signal corresponding to the first digital input signal; and in response a second digital input signal, a second switching network to couple a voltage produced across at least one of the first impedance elements to a second output node, the first impedance elements configured to produce a second analog signal corresponding to the second digital input signal, wherein the first output node and the second output node form multiple outputs.

This overview is intended to provide an overview of subject matter of the present patent application. It is not intended to provide an exclusive or exhaustive explanation of the invention. The detailed description is included to provide further information about the present patent application.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

This document describes, among other things, a multiple output, multiple impedance string, e.g., resistor string, digital-to-analog converter (DAC) circuit that can provide a first output having a first resolution, e.g., 12-bit resolution, and a second output having a second resolution different than the first resolution, e.g., 6-bit resolution. As described below with respect to FIGS. 1 and 2, a main impedance string and a secondary impedance string can be coupled using switching networks to provide a single DAC output. Using various techniques of this disclosure, by coupling additional switches to the main impedance string, an additional DAC output can be realized without the use of an additional impedance string, as seen in FIG. 3. In this manner, a multiple output DAC circuit can be formed by sharing an impedance string.

As mentioned above, an electrochemical (EC) sensor can be used for various applications, such as for sensing the presence of one or more constituent gases, such as oxygen, carbon monoxide, etc., in an environment around the electrochemical sensor. As a specific example, for a 3-lead EC sensor, the bias voltage requirement between its reference electrode and sensing electrode can be diverse, which can require a flexibility of both the common-mode voltage and differential voltage. In such applications, two independent DACs with low noise and low power are desirable.

The present inventors have recognized that one problem to be solved is providing a sensor solution system, for example, with a digital-to-analog converter (DAC) circuit that is both high-resolution and low-power. For example, it can be desirable to increase the resolution of a DAC of a sensor control system to reduce quantization noise, creating a smoother signal, and to improve accuracy improve accuracy. Increased DAC resolution, however, can result in the use of more switches to control, and thus more power consumption, particularly at higher temperatures due to leakage currents, for example. If a sensor is battery-powered, it can be desirable to lower power consumption. The present inventors have solved this problem by providing a multi-output DAC circuit that uses a shared impedance string, such as a resistor string, to generate multiple outputs having different resolutions, e.g., a first output at 12-bit resolution and a second output at a 6-bit resolution. Using a shared impedance string can form an intrinsic correlation between both outputs and also save power. The asymmetry of the output resolutions, e.g., 12-bit and 6-bit resolutions, is the result of using additional symmetry on one output to minimize overall circuitry, e.g., for lower power, reduction in area, increased speed, and higher temperature operation. These techniques can reduce circuit complexity, thereby reducing the cost and the size of the DAC circuit, as well as reducing the leakage current, which can reduce power consumption.

Figure 1:
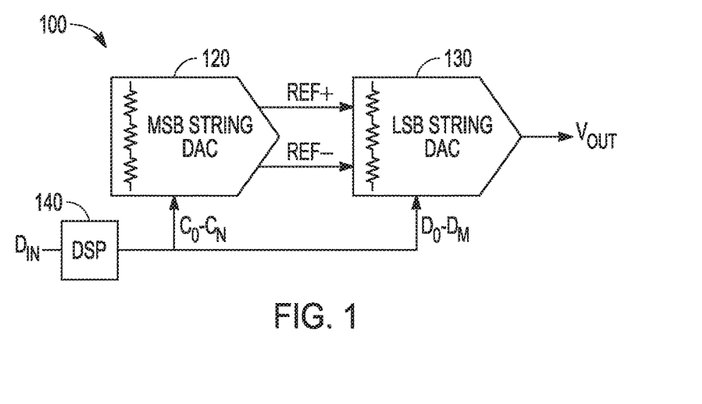
FIG. 1 depicts an example of a dual string digital-to-analog converter.

FIG. 1 shows a simplified block diagram of a dual string DAC 100. The dual string DAC 100 includes a most significant bits (MSB) String 120 and a least significant bits (LSB) String 130, which both include series-coupled impedance strings, such as resistor strings. A digital signal processor (DSP) 140 receives a digital input signal Din and outputs control signals $C_0$-$C_N$ to control the MSB String 120 and control signals $D_0$-$D_M$ to control the LSB String 130. The MSB String 120 typically converts the most significant bits (MSBs) of the digital word, and its output is coupled to the LSB String 130, which converts the least significant bits (LSBs) of the digital word. VOUT represents the converted analog signal.

Figure 2:
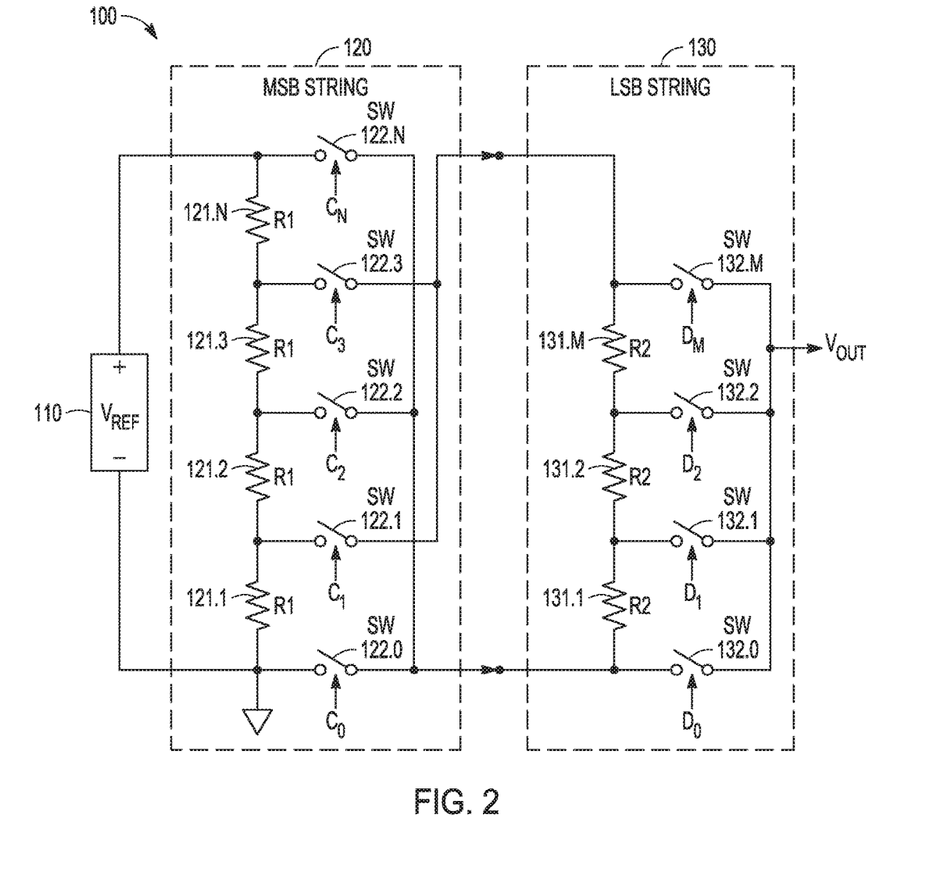
FIG. 2 depicts an example of a schematic diagram of the dual string digital-to-analog converter of FIG. 1.
Figure 3:
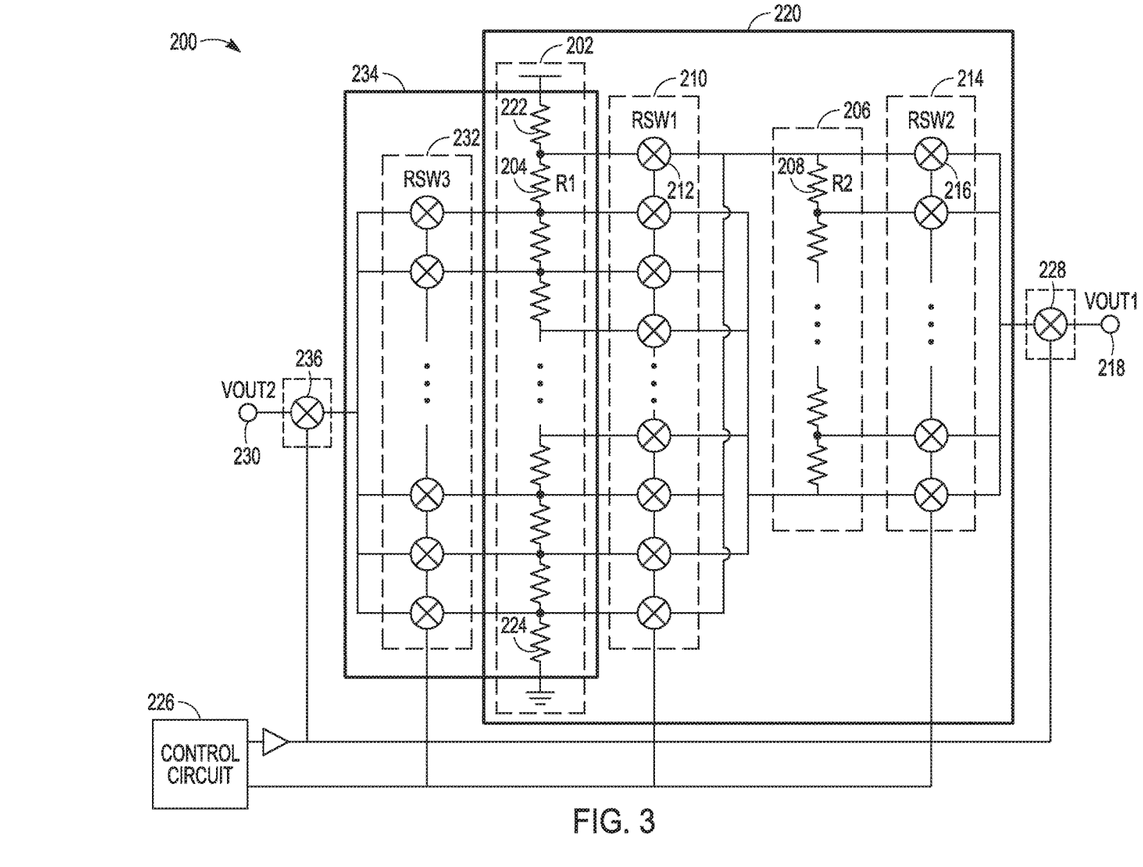
FIG. 3 is a schematic diagram showing an example of a multiple string, multiple output digital to analog converter circuit, in accordance with various techniques of this disclosure.

FIG. 2 depicts an example of a schematic diagram of the dual string digital-to-analog converter 100 of FIG. 1. As shown, each string 120, 130 include a resistor string 121.1-121.N, 131.1-131.M coupled to respective switch sets 122.0-122.N, 132.0-132.M that are operated according to digital word based control signals, $C_0$-$C_N$ and $D_0$-$D_M$. Also, the switches in switch sets 122.0-122.N, 132.0-132.M generally include only two states-on or off. The dual string DAC 100, however, is a single channel DAC. Multiple channel string DACs are disclosed in commonly assigned U.S. Pat. No. 9,124,296, the entire content of which is incorporated herein by reference. Multiple string DACs are disclosed in commonly assigned U.S. Pat. No. 9,100,045, the entire content of which is incorporated herein by reference. Another example of a multiple string DAC that can be used to implement the techniques of this disclosure is disclosed in commonly assigned U.S. Pat. No. 5,969,657, the entire content of which is incorporated herein by reference.

It will be appreciated that a multi-string DAC can also be considered a multi-stage DAC where at least two stages can include a string of impedance elements. In such a multi-string converter, a first stage uses a first string for converting an N-bit digital word, e.g., coarse conversion, and a second stage using a second string to further decode the N-bit digital word, e.g., finer conversion. Within the context of the following, which is provided to assist the person of skill in an understanding of features and benefits of an arrangement in accordance with the present teaching, each of the strings will be described with reference to an exemplary implementation using resistors. It will be appreciated that resistors are an example of the type of impedance element that may be used and it is not intended to limit the present teaching to an implementation where resistors are used exclusively as impedance elements. In this regard it will be appreciated that resistors may be a preferred type of impedance element, particularly in scenarios where the voltage across the string is high-such as the string that is coupled to the reference terminals of the converter. In other strings where the voltage is relatively small, other elements such as active MOS devices may also be used. The present teaching should therefore not be construed as being limited to a multi-resistor string DAC.

FIG. 3 is a schematic diagram showing an example of a multiple string, multiple output digital to analog converter circuit, in accordance with various techniques of this disclosure. The DAC circuit 200 can include a first impedance string 202, e.g., resistor string, including a plurality of first impedance elements 204, e.g., resistors, and a second impedance string 206, e.g., resistor string, including a plurality of second impedance elements 208, e.g., resistors. Each of the first impedance elements can have a first impedance, e.g., resistance, of R1. Each of the second impedance elements can have a second impedance, e.g., resistance, of R2. In some example implementations, impedance R1 can be different than impedance R2.

The DAC circuit 200 of FIG. 3 can include a first switching network RSW1 210 including a plurality of first switches 212 coupled to the first impedance string 202 and a second switching network RSW2 214 including a plurality of second switches 216 coupled to the second impedance string 206. The second switching network RSW2 can couple at least one of the second impedance elements to a first output node 218.

As seen in the example configuration of FIG. 3, every other switch 212 in the first switching network RSW1 can be coupled together. In the example configuration shown in FIG. 3, the switches in the first switching network RSW1 can be DC current carrying switches. The switches in the second switching network RSW1 can conduct substantially no DC current in normal operation and thus can be low leakage switches (or non-current carrying switches).

The first impedance string 202, e.g., the main impedance string, and the second impedance string 206, e.g., secondary impedance string, can generate a first analog signal VOUT1 at a first output node 218 that corresponds to a first digital input signal. The first analog signal VOUT1 can have a first resolution, e.g., 12-bit resolution, where the first impedance string 202 can be used to convert the MSBs of the first digital input signal and the second impedance string 206 can be used to convert the LSBs of the first digital input signal. The circuit components grouped in 220 can be considered to represent a first DAC.

In some example configurations, the first impedance string 202 can be coupled to the DAC reference terminal and ground via additional impedance elements 222, 224, e.g., resistors. These additional elements 222, 224 can be useful for range tuning and in low and ultra-low power applications for sub-threshold leakage reduction.

Similar to what was described above with respect to FIGS. 1 and 2, a control circuit 226, e.g., DSP, can receive a first digital input signal and output control signals to control respective switching networks 210, 214 to control the MSB String 202 and the LSB String 206 to generate the first analog signal VOUT1. More particularly, the DSP can control the first switching network 210 to couple a voltage produced across at least one of the first impedance elements 204 across the second impedance string 206 in response to the first digital input signal, where the digital input signal includes a digital bit stream, e.g., digital word, having MSBs and LSBs.

The impedance elements in the second impedance string 206 are configured to produce voltages in response to current passing from the first string 202 through the first switching network 210 to the second string 206 to produce a corresponding analog signal VOUT1 to the digital input signal to the first output node 218. In other words, the first and second impedance elements are configured to produce a first analog signal VOUT1 corresponding to the first digital input signal to the first output node 218.

In this manner, the DAC circuit 200 can provide a first analog output VOUT1, e.g., first DAC output, having a first resolution at the first output node 218 in response to a first digital input signal. As seen in FIG. 3, the first output node 218 can be coupled to an optional switch 228.

As mentioned above, this disclosure describes techniques to provide a second analog output VOUT2, e.g., second DAC output, in response to a second digital input signal, having a second resolution at a second output node 230, using a shared impedance string, e.g., the first impedance string 202. The shared impedance string 202 can be used to generate multiple outputs having different resolutions, e.g., a first DAC output VOUT1 at 12-bit resolution and a second DAC output VOUT2 at a 6-bit resolution. The circuit components grouped in 234 can be considered to represent a second DAC.

In the example configuration shown in FIG. 3, the control circuit 226, e.g., a DSP, can control a third switching network RSW3 232 to couple a voltage produced across at least one of the first impedance elements 204 in response to a second digital input signal, e.g., a 6-bit digital input signal. In this manner, the first impedance elements 204 can be configured to produce a second analog signal VOUT2 corresponding to the second digital input signal to a second output node 230. In other words, in the example configuration shown in FIG. 3, the first analog signal VOUT1 at the first output node 218 can correspond to the MSBs and the LSBs of a first digital input signal, and the second analog signal VOUT2 at the second output node 230 can correspond to a second digital input signal. As such, the DAC circuit 200 of FIG. 3 can be considered to include a first DAC 220 having a first resolution, e.g., 12-bit resolution, and a second DAC 234 having a second resolution, e.g., 6-bit resolution, where the first output node 218 and the second output node 230 form multiple DAC outputs.

As seen in FIG. 3, the second output node 230 can be coupled to an optional switch 236. In some example configurations, the resolutions of VOUT1 and VOUT2 are different, as in FIG. 3.

In some example implementations, the first analog signal VOUT1 and the second analog signal VOUT2 can be used single ended. In some example implementations, and as described in more detail below, the first analog signal VOUT1 and the second analog signal VOUT2 can be used quasi-differentially. A quasi-differential implementation is not fully symmetric as would be a fully differential implementation due to the differing resolutions.

The switches of the switching networks described in this disclosure can be implemented using transistors including, but not limited to, field-effect transistors (FETs), such as metal-oxide-semiconductor (MOS) FETs, FinFETs, gate-all-around (GAA) FETs, etc. The switches of the switching networks described in this disclosure can be implemented using microelectromechanical systems (MEMS) or nanoelectromechanical systems (NEMS). The circuits described in this disclosure can be integrated on an integrated circuit.

It should be noted that although the configuration of FIG. 3 depicts two outputs, this disclosure is not limited to such a configuration. Rather, the circuit 200 of FIG. 3 can be configured to provide more than two outputs.

Additional information on the operation of multiple string DACs can be found in commonly assigned U.S. Pat. Nos. 9,124,296 and 9,100,045, the entire content of each being incorporated herein by reference.

Figure 4:
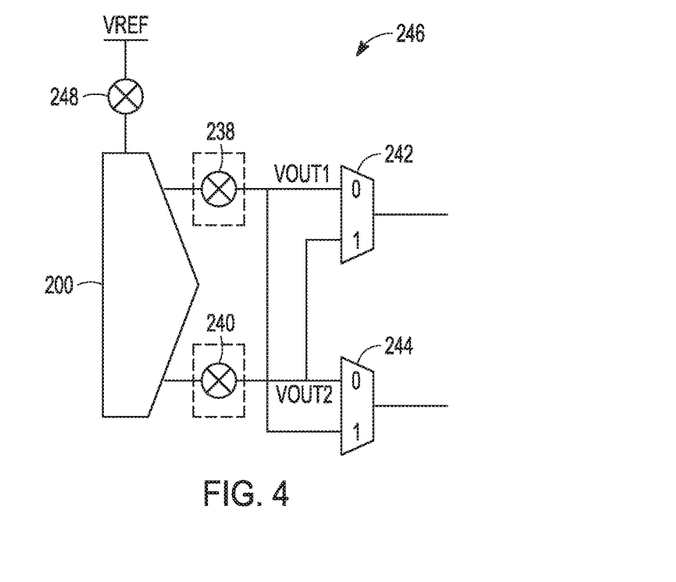
FIG. 4 is a schematic diagram showing an example of a multiplexer circuit configuration, in accordance with various techniques of this disclosure.

FIG. 4 is a schematic diagram showing an example of a multiplexer circuit configuration, in accordance with various techniques of this disclosure. In FIG. 4, the DAC circuit 200, e.g., of FIG. 3, can output two DAC outputs, namely the first analog signal VOUT1 and the second analog signal VOUT2. In the example shown, each of the two DAC outputs VOUT1 and VOUT2 can be coupled, e.g., via optional switches 238, 240, to both first and second multiplexers 242, 244. The internal configurations of the first and second multiplexers 242, 244 can allow the two DAC outputs VOUT1 and VOUT2 to be multiplexed, swapped, or chopped. A control circuit can control the first and second multiplexers 242, 244 of FIG. 4 to generate a pair of signals, including, for example, VOUT1/VOUT1, VOUT2/VOUT2, VOUT1/VOUT2, and VOUT2/VOUT1.

In some example configurations, the circuit 246 of FIG. 4 can include switch 248 coupled to the VREF terminal in this single ended example configuration, e.g., for power-down. It should be noted that FIG. 4 is a simplified functional representation. In some example configurations, it can be desirable to incorporate sample-and-hold (S/H) circuitry, additional low pass filtering circuitry, and to consider the parasitic load of both interconnect and load circuitry. Optional switches 238, 240 can be used for explicit sample-and-hold purposes as shown, enabling isolating DAC core settling activity. Similar functionality, but without isolation, can be achieved via switching networks RSW2 and RSW3 on their own, via merging digital switch controls. In some examples, the optional switches 238, 240 can be explicit switches, inside or outside the DAC core sub-block. The optional switches 238, 240 can be used for sample-and-hold or break-before-make (BBM) switching functions.

Figure 5:
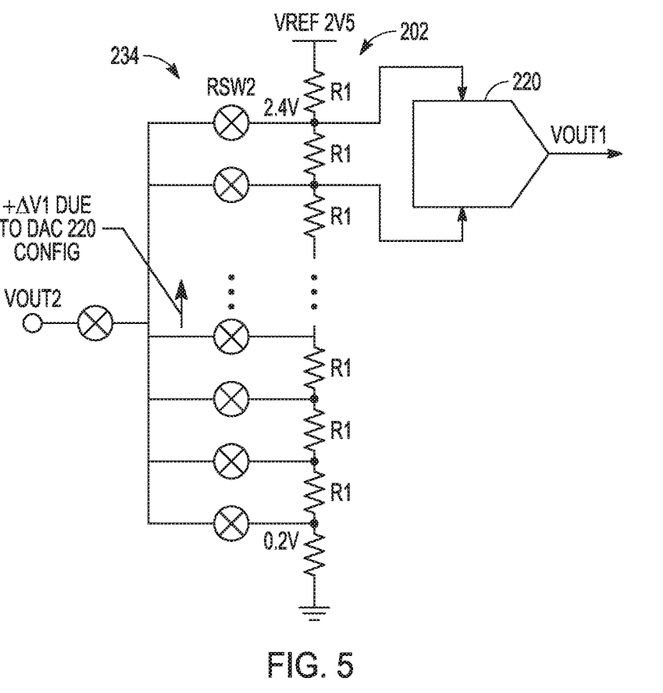
FIG. 5 is a schematic diagram showing an example of a multiple string, multiple output digital to analog converter circuit, in accordance with various techniques of this disclosure, with crosstalk between the two DACs.
Figure 6:
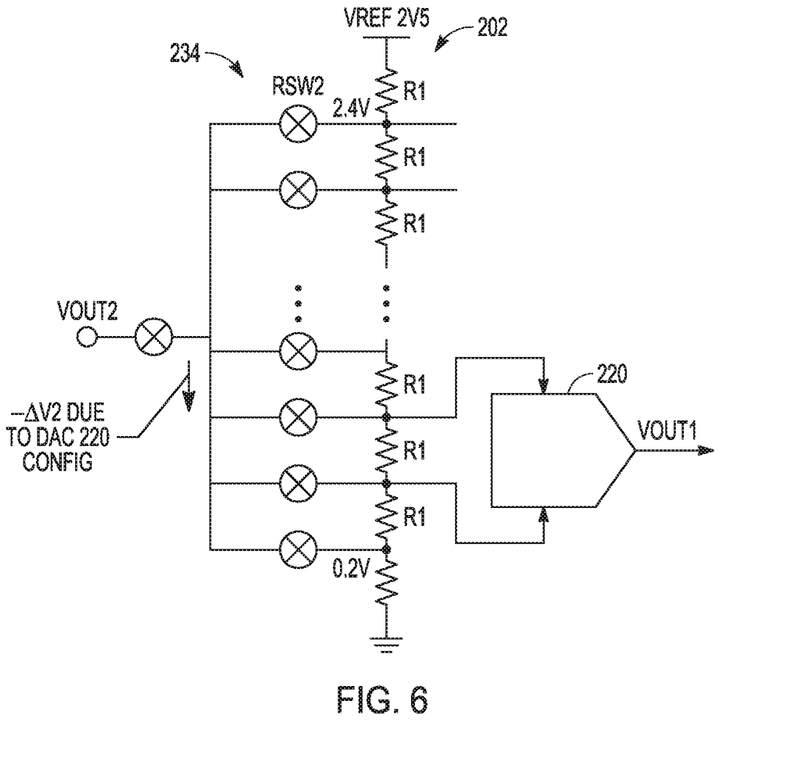
FIG. 6 is a schematic diagram showing another example of a multiple string, multiple output digital to analog converter circuit, in accordance with various techniques of this disclosure, with crosstalk between the two DACs.

By using a common impedance string to produce an additional separate, e.g., lower resolution, DAC output, the present inventors have recognized that one problem to be solved is an interaction mechanism (or "crosstalk") between the two DAC outputs (or channels) when buffers are not used to buffer DAC 220. FIGS. 5 and 6 depict schematic diagrams illustrating the crosstalk problem to be solved. The present inventors have recognized that sharing a common impedance string 202 can result in an interaction, or crosstalk, between the two DACs 220, 234, when buffers are not used to buffer DAC 220. Depending on the relative location of the two DAC outputs VOUT1 and VOUT2, when the second impedance string 206 is in parallel with any one of the impedance elements of the first impedance string 202, the second impedance string 206 can try to pull up or pull down the second DAC output VOUT2, e.g., the 6-bit output, because of the loading on the first string 202. The crosstalk between the DAC outputs is described below with respect to FIGS. 5 and 6.

FIG. 5 is a schematic diagram showing an example of a multiple string, multiple output digital to analog converter circuit, in accordance with various techniques of this disclosure, with crosstalk between the two DACs. More particularly, FIG. 5 is a simplified version of FIG. 3 of a first configuration in which the network of impedance elements of the first DAC 220 of FIG. 3 is above the network of impedance elements of the second DAC 234 of FIG. 3.

In FIG. 5, the first DAC 220, formed by the first impedance string 202 and the second impedance string 206 of FIG. 3, loads the first string 202. In this configuration in which first DAC 220 is above the network of impedance elements of the second DAC 234, the first DAC 220 can pull up the second DAC output VOUT2 by an amount $+\Delta V1$.

FIG. 6 is a schematic diagram showing another example of a multiple string, multiple output digital to analog converter circuit, in accordance with various techniques of this disclosure, with crosstalk between the two DACs. More particularly, FIG. 6 is a simplified version of FIG. 3 of a first configuration in which the network of impedance elements of the first DAC 220 of FIG. 3 is below the network of impedance elements of the second DAC 234 of FIG. 3.

In FIG. 6, the first DAC 220, formed by the first impedance string 202 and the second impedance string 206 of FIG. 3, loads the first string 202. In this configuration in which first DAC 220 is below the network of impedance elements of the second DAC 234, the first DAC 220 can pull down the second DAC output VOUT2 by an amount $-\Delta V2$.

The present inventors have resolved and substantially cancelled out the crosstalk problem by including a loading compensation circuit to selectively adjust a pull-up or a pull-down of one of the first and second impedance elements to compensate for a loading by the other of the first and second impedance elements. The known specifics of the DAC architecture and design can dictate the loading effects. Given that the DAC digital inputs can correspond to the position and loading of the DACs on the first impedance string, the relative location of the first and second DACs 220, 234 can be detected digitally. The present inventors have solved the problem using switched loading compensation circuit solutions that can be used to compensate for or substantially cancel out the DACs' relative code dependent, architecture and design dependent interaction above and below the cross-over threshold.

A control circuit, e.g., DSP, can digitally determine the relationship of the two DACs to one another, e.g., whether the first DAC 220 is above or below the second DAC 234. If the first DAC 220 is above the second DAC 234, the control circuit, e.g., control circuit 226 of FIG. 3, can control circuitry to pull down slightly, and if the first DAC 220 is below the second DAC 234, the control circuit can control circuitry to pull up slightly to compensate for loading effects.

Figure 7:
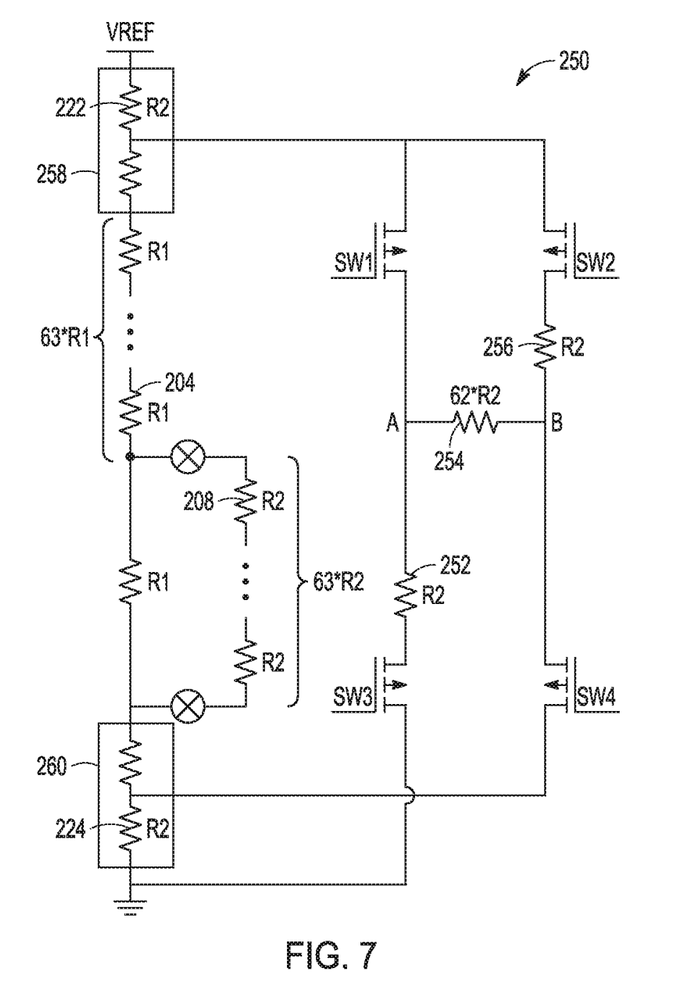
FIG. 7 is a schematic diagram showing an example of a switched impedance solution to reduce crosstalk between two DACs.

FIG. 7 is a schematic diagram showing an example of a switched impedance solution to reduce crosstalk between two DACs. In FIG. 7, a control circuit, e.g., control circuit 226 of FIG. 3, has controlled various switches in the first and second switching networks RSW1 210, RSW2 214 of FIG. 3 to close, resulting in the example configuration shown. The loading compensation circuit 250 of FIG. 7 can include additional switches, e.g., switches SW1-SW4, and additional impedance elements, 252, 254, and 256. The loading compensation circuit 250 is shown coupling into the impedances (of FIG. 3) between the DAC string terminals and the reference terminals (Vref+ and ground), above and below the DAC impedance string.

As mentioned above, the first impedance string 202 can be coupled to the DAC reference terminals and the ground via additional impedance elements 222, 224 of FIG. 3, e.g., resistors. The control circuit can control the switches SW1-SW4 to add impedance elements in parallel with the upper impedance element 222 or the lower impedance element 224 to cancel the loading effect.

In the example configuration shown in FIG. 7, one or more of either of the first and second impedance elements 204, 208 can be placed in parallel with the upper resistor divider 258 or lower resistor divider 260 by controlling the four switches SW1-SW4 to compensate for a loading by the other of the first and second impedance elements. In some example implementations, non-unit elements may be used. e.g., to save are. In the non-limiting specific example configuration shown in FIG. 7, second impedance elements R2 can be placed in parallel with the upper resistor divider 258 or lower resistor divider 260 using switches SW1-SW4. In this manner, the loading compensation circuit of FIG. 7 can be a passive solution to the crosstalk problem.

With specific reference to a multiple output DAC circuit with a first output having a 12-bit resolution and a second output having a 6-bit output resolution, a switch control signal can be generated from a dynamic comparison result of the 6 MSB of the 12-bit input code of the first digital signal (12 bit[11:0]) and the 6-bit input code of the second digital signal (6 bit[5:0]) to make sure the load effect of upper and lower resistor string is the same. The following example control logic can be used to control the switches in such a configuration:

if DAC 12 bit[11:6] is greater than or equal to DAC 6 bit[5:0], then SW1 and SW2 are OFF, and SW3 and SW4 are ON,
    DAC 12 bit[11:0] equals DAC 12 bit[11:0]+1; and
    if DAC 12 bit[11:0] equals the maximum value, then keep the value;
if DAC 12 bit[11:6] is less than DAC 6 bit[5:0], then SW1 and SW2 are ON, and SW3 and SW4 are OFF;
    DAC 12 bit[11:0] equals DAC 12 bit[11:0]−1; and
    if DAC 12 bit[11:0] equals the minimum value, then keep the value.

As seen above, the 12-bit DAC can add or subtract 1 to keep its original value after the anti-crosstalk function is enabled. In addition, the digital needs to know what to do for the maximum and minimum code of 12 bits. As a whole, after one more string resistor is added, the 12 bit DAC will be level shifted 2 LSB for its full scale. The disclosure is not limited to 12-bit and 6-bit digital input signals.

In some example configurations, break-before-make (BBM) switching can be used to avoid any shoot-through current that can otherwise occur when the SW1-SW4 data changes, due to differences in signal paths' delay as well as finite and variable turn on and off times. Impedance elements 252, 256 can be used to limit the current when discharging node A from close to VREF to ground and when charging node B from close to ground to VREF.

Figure 8:
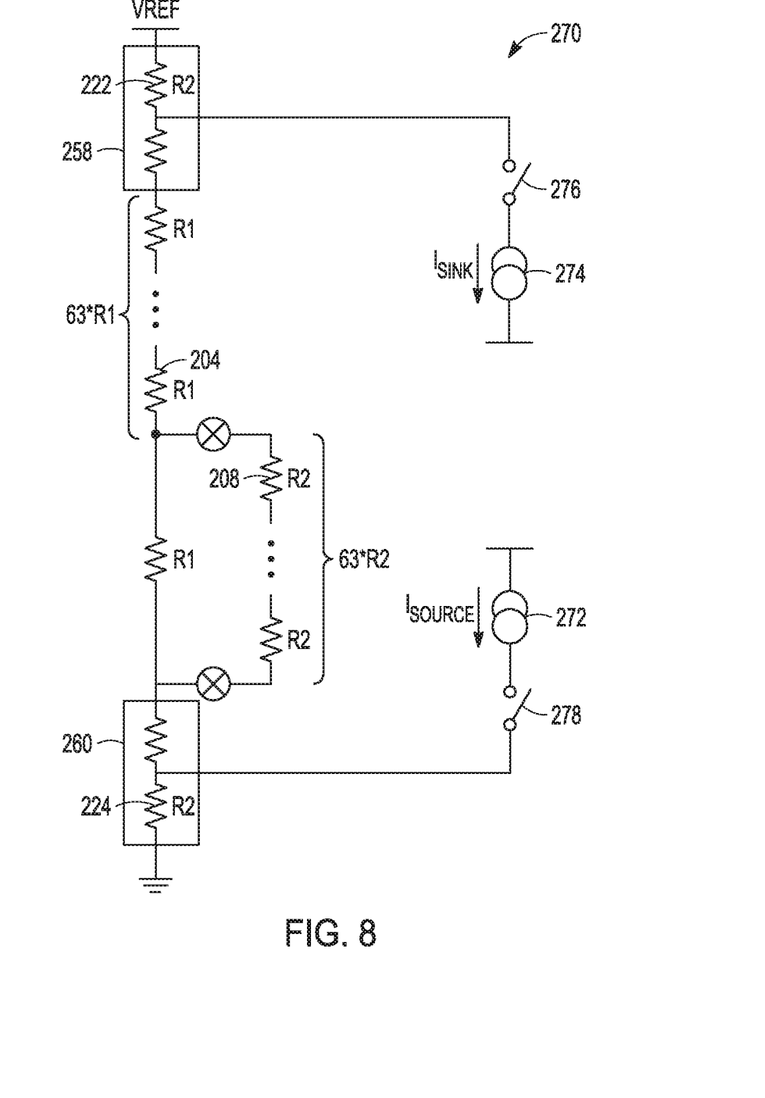
FIG. 8 is a schematic diagram showing an example of a switched current solution to reduce crosstalk between two DACs.

FIG. 8 is a schematic diagram showing an example of a switched current solution to reduce crosstalk between two DACs. In contrast to the passive configuration shown in FIG. 7, the loading compensation circuit 270 of FIG. 8 can be an active solution to the crosstalk problem. In particular, a switched current solution can be used to generate a current to effect an anti-crosstalk modulation similar to the switched impedance solution of FIG. 7. The loading compensation circuit 270 is shown coupling into the impedances (of FIG. 3) between the DAC string terminals and the reference terminals (Vref+ and ground), above and below the DAC impedance string.

Current sources and sinks are known to those of ordinary skill in the art, as are current mirrors, or current replicators. Current sources and current sinks are generally of one polarity and current mirrors can be used to make one current source/sink change polarity if desired, reflecting the current using a common-mode level. Alternately, a separate current source 272 and current sink 274 can be switched using a switching network having switches 276, 278 to achieve the same function, as shown in the example loading compensation circuit 270 of FIG. 8.

In some example implementations, a current source or current sink sub-block may use the same voltage reference levels and the same impedance material or use a unit resistor as the DAC networks to enable tracking with the reference levels and impedance value, e.g., resistor value, tracking with variation such as process and temperature.

To provide loading compensation, e.g., to pull up or pull down the circuitry, a switched current sink 274 can be coupled above the DAC at the upper resistor divider 258 and a switched current source 272 can be coupled below the DAC at the lower resistor divider 260, as shown in FIG. 8. In other example configurations, the switched current sink 274 and the switched current source 272 can be coupled to one or more nodes within the DAC. Some example configurations can include aspects of both the loading compensation circuits of FIGS. 7 and 8, e.g., both switched impedance and switched current solutions.

A person of ordinary skill will understand that a current source can output positive or negative current to perform a source or sink function. As such, it will be appreciated that a current source can be used generally to describe a high impedance current output element that outputs positive or negative current.

Figure 9:
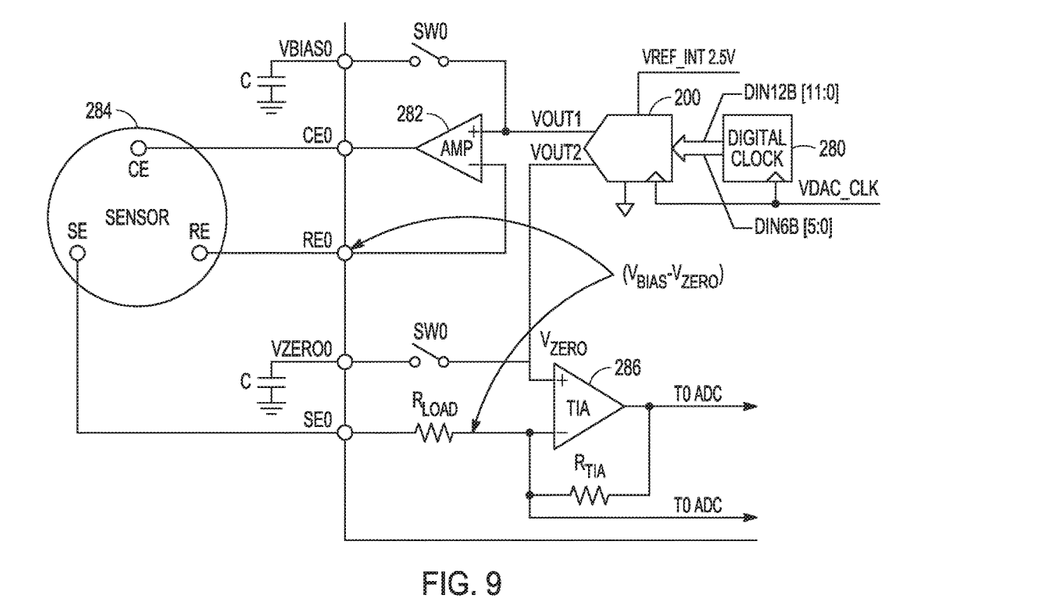
FIG. 9 is a schematic diagram showing an example of an application of the multiple string, multiple output DAC circuit of FIG. 3, in accordance with various techniques of this disclosure.

FIG. 9 is a schematic diagram showing an example of an application of the multiple string, multiple output DAC circuit 200 of FIG. 3, in accordance with various techniques of this disclosure. The DAC circuit 200 (of FIG. 3) can receive digital input signals from digital control unit 280. For example, the DAC circuit 280 can receive a first digital input signal, e.g., 12-bit digital input signal DIN12b[11:0], and a second digital input signal, e.g., 6-bit digital input DIN6b[5:0], and output respective analog output signals VOUT1 and VOUT2 having first and second resolutions. The first analog output signal VOUT1 can be provided to a non-inverting input of an amplifier 282, the output of which providing an excitation signal to a first electrode of a sensor 284, such as to the counter electrode (CE). An inverting input of the amplifier 282 can be coupled to a second electrode of the sensor 284, such as a reference electrode RE. The sensor 284 can be, for example, an electrochemical sensor used for various applications, such as for sensing the presence of one or more constituent gases, such as oxygen, carbon monoxide, etc., in an environment around the electrochemical sensor.

The second analog output signal VOUT2 can be provided to a non-inverting input of a transimpedance amplifier 286. An inverting input of the transimpedance amplifier 286 can receive an output current of a sensing electrode (SE) of the sensor 284. An inverting input of the transimpedance amplifier 286 can be coupled to the sensing electrode (SE) of the sensor 284 by, for example, a load resistor $R_{LOAD}$, or otherwise. The transimpedance amplifier 286 can be configured with a feedback resistor, $R_{TIA}$, in a feedback path between the output of the transimpedance amplifier 286 and the inverting input of the transimpedance amplifier 286. The output of the transimpedance amplifier 286 and the input to the inverting terminal of the transimpedance amplifier 286 can be coupled to an analog-to-digital converter (ADC) (not shown).

Figure 10:
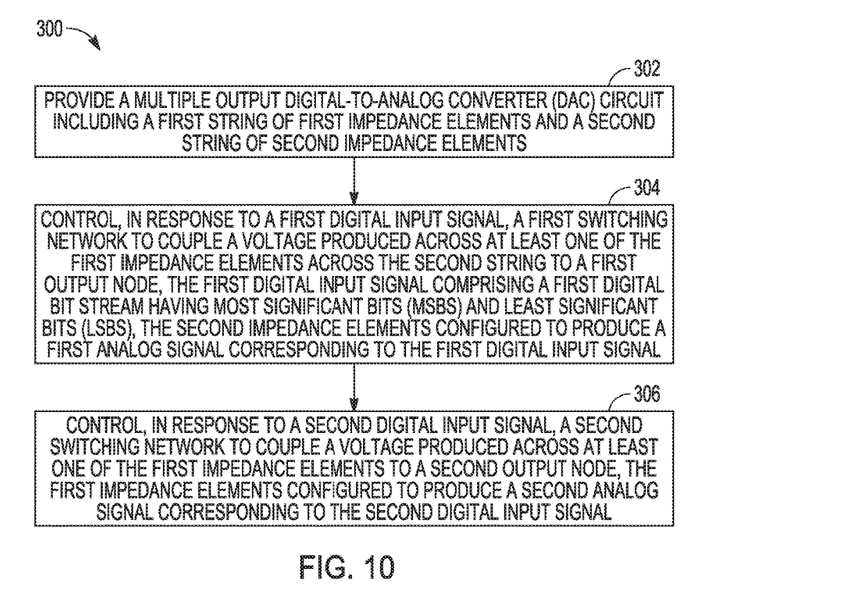
FIG. 10 is an example of a flow diagram of a method of converting a first digital input string to a corresponding first analog signal having a first resolution and converting a second digital input string to a corresponding second analog signal having a second resolution, in accordance with this disclosure.

FIG. 10 is an example of a flow diagram of a method 300 of converting a first digital input string to a corresponding first analog signal having a first resolution and converting a second digital input string to a corresponding second analog signal having a second resolution, in accordance with this disclosure. At block 302, the method 300 can include providing a multiple output digital-to-analog converter (DAC) circuit, the DAC circuit comprising a first string, e.g., string 202 of FIG. 3, of first impedance elements and a second string, e.g., string 206 of FIG. 3, of second impedance elements.

At block 304, the method 300 can include controlling, in response to a first digital input signal, a first switching network to couple a voltage produced across at least one of the first impedance elements across the second string to a first output node, the first digital input signal comprising a first digital bit stream having most significant bits (MSBs) and least significant bits (LSBs), the second impedance elements configured to produce a first analog signal corresponding to the first digital input signal. For example, a control circuit, e.g., control circuit 226 of FIG. 3, can control the first switching network 210 to couple a voltage produced across at least one of the impedance elements in the first string 202 across the second string 206 in response to a first digital input signal, e.g., a 12-bit signal. The impedance elements of the first string 202 and the second string 206 can produce a first analog signal VOUT1 corresponding to the first digital input signal.

At block 304, the method 300 can include controlling, in response to a second digital input signal, a second switching network to couple a voltage produced across at least one of the first impedance elements to a second output node, the first impedance elements configured to produce a second analog signal corresponding to the second digital input signal, where the first output node and the second output node form multiple outputs. For example, a control circuit, e.g., control circuit 226 of FIG. 3, can control the second switching network 232 to couple a voltage produced across at least one of the impedance elements of the first string 202 to the second output node 230 in response to a second digital input signal, e.g., a 6-bit signal, to produce a second analog signal VOUT2 corresponding to the second digital input signal.

The method 300 of FIG. 10 can optionally further include controlling a loading compensation circuit to selectively adjust a pull-up or a pull-down of one of the first and second impedance elements to compensate for a loading by the other of the first and second impedance elements. In some example implementations, controlling the loading compensation circuit can include providing one or more anti-crosstalk impedance elements, and controlling a third switching network to couple the one or more anti-crosstalk impedance elements in parallel with at least one of the second impedance elements. In other example implementations, controlling the loading compensation circuit can include providing at least one current source, and controlling a third switching network to couple the at least one current source to the second string. In some example implementations, controlling the loading compensation circuit can include controlling the loading compensation circuit using a comparison between the MSBs of the first digital input signal and the second digital input signal.

The method 300 of FIG. 10 can optionally further include controlling a fourth switching network, e.g., switching network RSW2 of FIG. 3, to couple at least one of the second impedance elements to the first output node.

The method 300 of FIG. 10 can optionally further include providing a first multiplexer having a first input and a second input, providing a second multiplexer having a first input and a second input, where the first input of the first multiplexer is coupled to the first output node and configured to receive the first analog signal, where the first input of the second multiplexer is coupled to the second output node and configured to receive the second analog signal, where the first input of the first multiplexer is coupled to the second input of the second multiplexer, and where the first input of the second multiplexer is coupled to the second input of the first multiplexer, and controlling the first and second multiplexers to output a pair of signals.

VARIOUS NOTES

Each of the non-limiting aspects or examples described herein may stand on its own, or may be combined in various permutations or combinations with one or more of the other examples.

The above detailed description includes references to the accompanying drawings, which form a part of the detailed description. The drawings show, by way of illustration, specific embodiments in which the invention may be practiced. These embodiments are also referred to herein as "aspects" or "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact discs and digital video discs), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

What is claimed is:

1. A multiple output digital-to-analog converter (DAC) circuit providing at least two analog output signals of different resolution, the DAC circuit comprising:
   a first string of first impedance elements;
   a second string of second impedance elements coupled in parallel with the first string;
   in response to a first digital input signal, a first switching network to couple a voltage produced across at least one of the first impedance elements across the second string to a first output node, the first digital input signal comprising a first digital bit stream having most significant bits (MSBs) and least significant bits (LSBs), the second impedance elements configured to produce a first analog signal corresponding to the first digital input signal; and
   in response a second digital input signal, a second switching network to couple a voltage produced at one of the first impedance elements to a second output node, the first impedance elements configured to produce a second analog signal corresponding to the second digital input signal,
   wherein the first output node and the second output node form multiple outputs.

2. The DAC circuit of claim 1, the circuit comprising:
   a loading compensation circuit to selectively adjust a pull-up or a pull-down of one of the first and second impedance elements to compensate for a loading by the other of the first and second impedance elements.

3. The DAC circuit of claim 2, wherein the loading compensation circuit includes:
   one or more anti-crosstalk impedance elements; and
   a third switching network to couple the one or more anti-crosstalk impedance elements in parallel with at least one of the second impedance elements.

4. The DAC circuit of claim 2, wherein the loading compensation circuit includes:
   at least one current source; and
   a third switching network to couple the at least one current source to the second string.

5. The DAC circuit of claim 2, comprising:
   a control circuit configured to control the loading compensation circuit using a comparison between the MSBs of the first digital input signal and the second digital input signal.

6. The DAC circuit of claim 1, comprising:
   a first multiplexer having a first input and a second input; and
   a second multiplexer having a first input and a second input,
   wherein the first input of the first multiplexer is coupled to the first output node and configured to receive the first analog signal,
   wherein the first input of the second multiplexer is coupled to the second output node and configured to receive the second analog signal,
   wherein the first input of the first multiplexer is coupled to the second input of the second multiplexer, and wherein the first input of the second multiplexer is coupled to the second input of the first multiplexer.

7. The DAC circuit of claim 1, wherein the first impedance elements include first resistors, each of the first resistors having a first resistance, wherein the second impedance elements include second resistors, each of the second resistors having a second resistance.

8. The DAC circuit of claim 1, comprising:
   a fourth switching network to couple at least one of the second impedance elements to the first output node.

9. The DAC circuit of claim 1, wherein the first output node is an output node of a first DAC, wherein the second output node is an output node of a second DAC, and wherein the first DAC and the second DAC share the first string.

10. A method of converting a first digital input string to a corresponding first analog signal having a first resolution and converting a second digital input string to a corresponding second analog signal having a second resolution, the method comprising:
   providing a multiple output digital-to-analog converter (DAC) circuit, the DAC circuit comprising a first string of first impedance elements and a second string of second impedance elements coupled in parallel with the first string;

controlling, in response to a first digital input signal, a first switching network to couple a voltage produced across at least one of the first impedance elements across the second string to a first output node, the first digital input signal comprising a first digital bit stream having most significant bits (MSBs) and least significant bits (LSBs), the second impedance elements configured to produce a first analog signal corresponding to the first digital input signal; and controlling, in response to a second digital input signal, a second switching network to couple a voltage produced at one of the first impedance elements to a second output node, the first impedance elements configured to produce a second analog signal corresponding to the second digital input signal, wherein the first output node and the second output node form multiple outputs.

11. The method of claim 10, further comprising:
controlling a loading compensation circuit to selectively adjust a pull-up or a pull-down of one of the first and second impedance elements to compensate for a loading by the other of the first and second impedance elements.

12. The method of claim 1, wherein controlling the loading compensation circuit comprises:
providing one or more anti-crosstalk impedance elements; and
controlling a third switching network to couple the one or more anti-crosstalk impedance elements in parallel with at least one of the second impedance elements.

13. The method of claim 11, wherein controlling the loading compensation circuit comprises:
providing at least one current source; and
controlling a third switching network to couple the at least one current source to the second string.

14. The method of claim 11, wherein controlling the loading compensation circuit comprises:
controlling the loading compensation circuit using a comparison between the MSBs of the first digital input signal and the second digital input signal.

15. The method of claim 10, comprising:
controlling a fourth switching network to couple at least one of the second impedance elements to the first output node.

16. The method of claim 10, comprising:
providing a first multiplexer having a first input and a second input; and
providing a second multiplexer having a first input and a second input,
wherein the first input of the first multiplexer is coupled to the first output node and configured to receive the first analog signal,
wherein the first input of the second multiplexer is coupled to the second output node and configured to receive the second analog signal,
wherein the first input of the first multiplexer is coupled to the second input of the second multiplexer, and wherein the first input of the second multiplexer is coupled to the second input of the first multiplexer; and
controlling the first and second multiplexers to output a pair of signals.

17. An electrochemical sensing circuit comprising:
a multiple output digital-to-analog converter (DAC) circuit providing at least two analog output signals of different resolution, the DAC circuit comprising:
a first string of first impedance elements;
a second string of second impedance elements;
in response to a first digital input signal, a first switching network to couple a voltage produced across at least one of the first impedance elements across the second string to a first output node, the first digital input signal comprising a first digital bit stream having most significant bits (MSBs) and least significant bits (LSBs), the second impedance elements configured to produce a first analog signal corresponding to the first digital input signal; and
in response a second digital input signal, a second switching network to couple a voltage produced at one of the first impedance elements to a second output node, the first impedance elements configured to produce a second analog signal corresponding to the second digital input signal,
wherein the first output node and the second output node form multiple outputs; and
an electrochemical sensor coupled to at least one of the first output node and the second output node.

18. The electrochemical sensing circuit of claim 17, wherein the DAC circuit comprises:
a loading compensation circuit to selectively adjust a pull-up or a pull-down of one of the first and second impedance elements to compensate for a loading by the other of the first and second impedance elements.

19. The electrochemical sensing circuit of claim 18, wherein the loading compensation circuit includes:
one or more anti-crosstalk impedance elements; and
a third switching network to couple the one or more anti-crosstalk impedance elements in parallel with at least one of the second impedance elements.

20. The electrochemical sensing circuit of claim 18, wherein the loading compensation circuit includes:
at least one current source; and
a third switching network to couple the at least one current source to the second string.

* * * * *

UNITED STATES PATENT AND TRADEMARK OFFICE
CERTIFICATE OF CORRECTION

PATENT NO. : 9,941,894 B1  
APPLICATION NO. : 15/586848  
DATED : April 10, 2018  
INVENTOR(S) : Gu et al.

Page 1 of 1

It is certified that error appears in the above-identified patent and that said Letters Patent is hereby corrected as shown below:

On the Title Page

On page 2, in Column 1, under "Other Publications", Line 1, delete "Metter" and insert --Meter-- therefor On page 2, in Column 1, under "Other Publications", Line 4, delete "Cicuit"," and insert --Circuit",-- therefor In the Claims In Column 15, Line 23, in Claim 12, delete "claim 1," and insert --claim 11,-- therefor Signed and Sealed this  
Twenty-eighth Day of May, 2019

Andrei Iancu  
*Director of the United States Patent and Trademark Office*